(12) United States Patent
Manginell et al.

(10) Patent No.: US 6,527,835 B1
(45) Date of Patent: Mar. 4, 2003

(54) CHEMICAL PRECONCENTRATOR WITH INTEGRAL THERMAL FLOW SENSOR

(75) Inventors: Ronald P. Manginell, Albuquerque, NM (US); Gregory C. Frye-Mason, Cedar Crest, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 10/029,341

(22) Filed: Dec. 21, 2001

(51) Int. Cl.[7] .......................... B01D 53/04; B01D 15/08
(52) U.S. Cl. .......................... 96/102; 96/108; 96/112; 96/146; 96/154; 55/524; 73/204.26
(58) Field of Search .......................... 95/82, 87, 89, 95/90, 116, 148; 96/4, 11, 101, 102, 105, 126, 143, 146, 154, 108–116; 55/524, DIG. 5; 73/204.25, 204.26, 204.27

(56) References Cited

U.S. PATENT DOCUMENTS

| | | | | |
|---|---|---|---|---|
| 4,433,982 A | * | 2/1984 | Odernheimer et al. | 55/158 |
| 4,599,095 A | * | 7/1986 | Barnes et al. | 55/208 |
| 4,891,977 A | * | 1/1990 | Johnson et al. | 73/204.26 |
| 5,087,275 A | * | 2/1992 | Pribat et al. | 55/386 |
| 5,151,110 A | * | 9/1992 | Bein et al. | 55/75 |
| 5,224,972 A | * | 7/1993 | Frye et al. | 55/18 |
| 5,251,481 A | * | 10/1993 | Huck et al. | 73/204.26 |
| 5,388,457 A | | 2/1995 | Yasui | 73/204.26 |
| 5,464,966 A | | 11/1995 | Gaitan et al. | 219/544 |
| 5,467,649 A | * | 11/1995 | Reihlen et al. | 73/204.26 |
| 5,501,893 A | * | 3/1996 | Laermer et al. | 428/161 |
| 5,589,396 A | * | 12/1996 | Frye et al. | 436/73 |
| 5,623,097 A | | 4/1997 | Horiguchi et al. | 73/204.15 |
| 5,703,287 A | * | 12/1997 | Treutler et al. | 73/204.26 |
| 5,705,745 A | * | 1/1998 | Treutler et al. | 73/204.26 |
| 5,720,798 A | * | 2/1998 | Nickerson et al. | 96/102 |
| 5,770,275 A | * | 6/1998 | Raman et al. | 427/535 |
| 5,880,354 A | * | 3/1999 | Newman et al. | 73/25.01 |
| 5,939,614 A | * | 8/1999 | Walters et al. | 73/23.39 |
| 6,079,265 A | * | 6/2000 | Wienand et al. | 73/204.26 |
| 6,171,378 B1 | | 1/2001 | Manginell et al. | 96/143 |
| 6,349,596 B1 | * | 2/2002 | Nakada et al. | 73/204.26 |
| 6,378,365 B1 | * | 4/2002 | Tu | 73/204.26 |
| 6,393,907 B1 | * | 5/2002 | Yamakawa et al. | 73/204.26 |
| 6,425,287 B1 | * | 7/2002 | Tominaga et al. | 73/204.26 |

OTHER PUBLICATIONS

Moser, et al., "A High Sensitivity CMOS Gas Flow Sensor on a Thin Dielectric Membrane," *Sensors and Actuators A*, 37–38 (1993), 33–37.

Bosman, et al., "Integrated Smart Two–Dimensional Thermal Flow Sensor with Seebeck–Voltage–to–Frequency Conversion," *Sensors and Actuators A*, 31 (1992), 9–16.

Li Qiu, et al., "A Microsensor with Integrated Heat Sink and Flow Guide for Gas Flow Sensing Applications," Transducers '95. Eurosensors IX, The 8th International Conference on Solid State Sensors and Actuators and Eurosensors IX, Stockholm, Sweden, Jun. 25–29, 1995.

* cited by examiner

Primary Examiner—Robert H. Spitzer
(74) Attorney, Agent, or Firm—Kevin W. Bieg

(57) ABSTRACT

A chemical preconcentrator with integral thermal flow sensor can be used to accurately measure fluid flow rate in a microanalytical system. The thermal flow sensor can be operated in either constant temperature or constant power mode and variants thereof. The chemical preconcentrator with integral thermal flow sensor can be fabricated with the same MEMS technology as the rest of the microanlaytical system. Because of its low heat capacity, low-loss, and small size, the chemical preconcentrator with integral thermal flow sensor is fast and efficient enough to be used in battery-powered, portable microanalytical systems.

18 Claims, 8 Drawing Sheets

CHEMICAL PRECONCENTRATOR WITH INTEGRAL THERMAL FLOW SENSOR

STATEMENT OF GOVERNMENT INTEREST

This invention was made with Government support under contract no. DE-AC04-94AL85000 awarded by the U.S. Department of Energy to Sandia Corporation. The Government has certain rights in the invention.

BACKGROUND OF THE INVENTION

The present invention relates generally to flow measurement in chemical analysis systems and, more particularly, to a chemical preconcentrator with an integral thermal flow sensor for flow measurement in a microanalytical system.

Portable, handheld microanalytical systems, which have been termed "chemical laboratories on a chip," are being developed to enable the rapid and sensitive detection of particular chemicals, including pollutants, high explosives, and chemical and biological warfare agents. These microanalytical systems should provide a high chemical selectivity to discriminate against potential background interferents and the ability to perform the chemical analysis on a short time scale with high selectivity. In addition, low electrical power consumption is needed for prolonged field use.

Current gas-phase microanalytical systems are based on gas chromatography (GC). Such microanalytical systems can also include a chemical preconcentrator. The chemical preconcentrator serves the important function of concentrating and purifying a chemical sample on a sorptive material at the inlet of the microanalytical system. The chemical preconcentrator can deliver an extremely sharp sample plug (<200 msec full-width at half maximum) to the downstream gas chromatograph by taking advantage of the rapid, efficient heating of the sorped chemical sample with a low-heat capacity, low-loss microhotplate.

Knowledge of the fluid flow rate in a microanalytical system is often required for an accurate interpretation of the system's response to a chemical species. For example, the retention time for chemical species depends directly on the gas flow rate in the microfabricated GC column. In addition, knowledge of the flow rate during sample collection is important to determine the total volume of gas that was sampled. This is information that can provide accurate determination of the concentration of analyte in the sampled gas. Finally, the height per theoretical plate obtained for microfabricated GC columns varies with gas flow rate. Therefore, the proper interpretation of results obtained with a microanalytical system containing a microfabricated GC depends critically on the knowledge of the gas flow rate during the time in which the chromatogram was taken.

Microfabricated thermal flow sensors have been developed that rely on the measurement of forced-convective heat loss from a heated element placed in the flow stream. See, e.g., M. Elwenspoek and R. Wiegerink, *Mechanical Microsensors,* Springer-Verlag, Berlin (2001). In a thermal-anemometer-type flow sensor, an element having a temperature-dependent resistivity is heated in a flow field. The heated element is typically a free-standing, thermally isolated structure that can function as a thermal flow sensor. Any flow across the heated element will increase the heat loss from the element due to forced convection. Thus, the larger the flow velocity is, the more heat will be lost from the heated element. The thermal flow sensor can be operated in a constant voltage or power mode wherein the temperature of the heated element is measured as the flow over the sensor is varied. With increased gas flow, the increased heat loss will lead to a reduction in the temperature of the element. The resulting decrease in the element's resistance can be measured with electrical instrumentation and related back to the flow velocity over the element. Alternatively, the thermal flow sensor can be operated in a constant temperature mode wherein the power needed to keep the temperature of the element constant in a fluid field is measured.

The thermal-anemometer-type flow sensor is ideally suited for microelectromechanical systems (MEMS). Such MEMS-based thermal flow sensors have the advantages of high precision, small size, low power consumption, high sensitivity, low response time, and batch production. In particular, such MEMS-based thermal flow sensors can be easily integrated with microanalytical systems because the same microfabrication technology can be used to construct all components of the microanalytical system, including the thermal flow sensor.

The chemical preconcentrator with integral thermal flow sensor of the present invention achieves the goals of accurately measuring the fluid flow rate in a microanalytical system while retaining system portability and functionality. The thermal flow sensor can be fabricated with the same MEMS technology as the rest of the microanalytical system, enabling easy integration with other microanalytical system components and the necessary control and sense electronics. Moreover, the same electronics that are used for desorption control of the chemical preconcentrator can be used to sense flow over it. Because this is a low-heat capacity, low-loss, miniature thermal flow sensor, it is fast and efficient enough to be used in battery-powered, portable systems.

SUMMARY OF THE INVENTION

The present invention comprises a chemical preconcentrator with integral thermal flow sensor. The chemical preconcentrator has a substrate having a suspended membrane formed thereon and at least one resistive heating element, comprising an electrically-conductive material whose resistance varies with temperature, disposed on a surface of the suspended membrane, and wherein the suspended membrane is exposed to a flow channel of the chemical preconcentrator. The thermal flow sensor can have a control circuit for heating the resistive heating element to a set temperature and measuring the power required to maintain the resistive heating element at the set temperature when a fluid flows in the flow channel. Alternatively, the control circuit can apply a set voltage across the resistive heating element and measure the resistance of the resistive heating element when a fluid flows in the flow channel.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

FIG. 1a shows the resistive heating element disposed on the side of the suspended membrane exposed to a flow channel of the chemical preconcentrator. FIG. 1b shows the resistive heating element disposed on the side of the suspended membrane opposite the flow channel.

DETAILED DESCRIPTION OF THE INVENTION

Figure 1A:
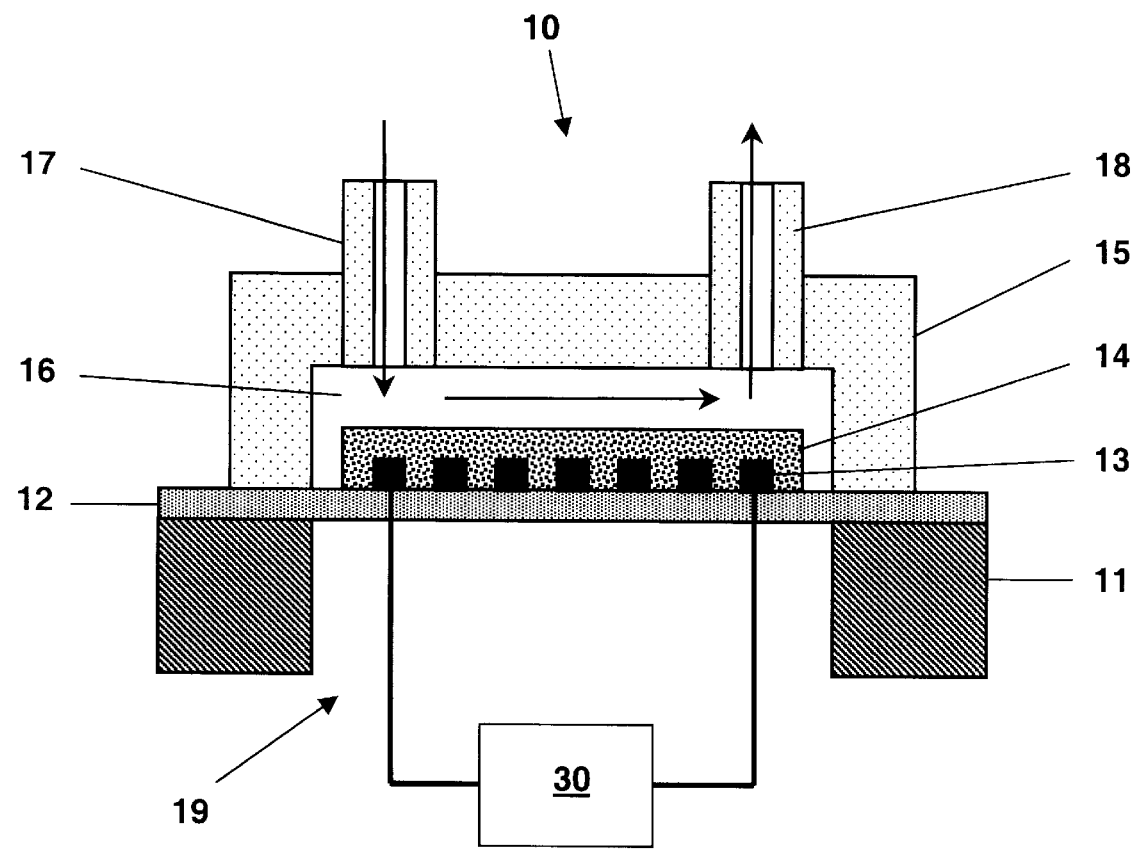
FIGS. 1a and 1b show schematic illustrations of different embodiments of a chemical preconcentrator having a resistive heating element disposed on a suspended membrane that provides an integral thermal flow sensor.
Figure 1B:
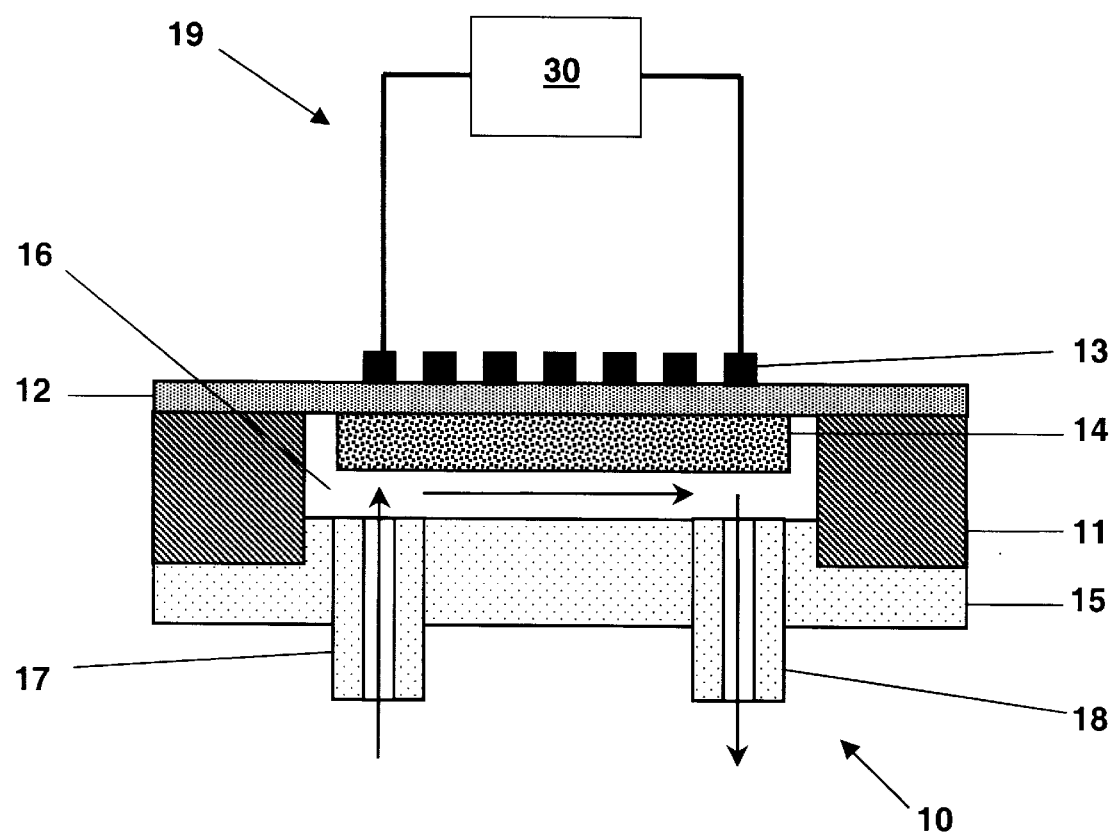

A chemical preconcentrator can serve the dual purpose of a preconcentration stage and a thermal flow sensor for microanalytical systems. FIGS. 1a and 1b show different embodiments of a chemical preconcentrator 10 that can be used with a microanalytical system as disclosed by Manginell and Frye-Mason in U.S. Pat. No. 6,171,378, which is incorporated herein by reference. The chemical preconcentrator 10 can accumulate chemical species of interest to be concentrated in a small area for subsequent sudden release by thermal desorption to a downstream GC or other analytical instrument. The chemical preconcentrator 10 has a very small heat capacity to allow very rapid heating and release of the concentrated chemical species for improved detectability. The small heat capacity and thermal conductivity of the chemical preconcentrator 10 also enables high flow sensitivity and low response time when a resistive heating element 13 is used as a thermal flow sensor 19, according to the present invention.

The chemical preconcentrator 10 can comprise a substrate 11 having a suspended membrane 12 formed thereon, a resistive heating element 13 disposed on a surface of the membrane 12, and a sorptive material 14 disposed on a surface of the membrane 12 to sorb and concentrate a chemical species of interest from a vapor. The chemical preconcentrator 10 can be constructed by microfabrication techniques disclosed by Manginell and Frye-Mason.

The substrate 11 can comprise a semiconductor (e.g., silicon) or a dielectric (e.g., glass). The membrane 12 can comprise a material having low thermal conductivity, such as silicon nitride. The membrane 12 can be a few millimeters on a side and can also be thin (e.g., 0.5 $\mu$m total thickness) to minimize its heat capacity and reduce thermal conduction to the substrate 11. The resistive heating element 13 can be formed by deposition of one or more layers of an electrically-conductive material, such as platinum metal, over the membrane 12 and patterning the layers of the metal to form a circuitous or serpentine metal trace. The metal trace can have a thickness of about 100 nm and can generally cover about 50% of the area of the suspended membrane 12. The sorptive material 14 can comprise a thin (about 1–100 $\mu$m) layer of a material, such as a polymer, microporous material, or a sol-gel oxide, that selectively sorbs the chemical species of interest from the vapor. The sorptive material 14 can also comprise particles that are attached to the suspended membrane 12, these particles acting to selectively sorb the chemical species of interest from the vapor.

Finally, the chemical preconcentrator 10 can be fixtured with an attached lid 15 having an etched flow channel 16 and capillary tubes for gas inlet 17 and gas outlet 18. The lid 15 can be made from materials such as glass, polymers, or metals. The flow channel 16 in the lid 15 can be produced by conventional grinding or etching or by techniques that reproduce structures, such as hot embossing. The flow channel 16 can be generally as wide as the chemical preconcentrator 10, about 2.5 mm, and can be about 100 $\mu$m deep. The capillaries 17, 18 can be epoxied into the lid 15 to allow gas to flow into the channel 16, over the sorptive material 14, and out of the lid 15.

The resistive heating element 13 can provide a thermal flow sensor 19 when it is connected to an electronic control circuit 30 for controlling the voltage applied to or temperature of the resistive heating element 13. When the resistive heating element 13 is operated as a thermal anemometer, the thermal flow sensor 19 can have high sensitivity to flow variations because heat loss to the flowing gas dominates over heat loss to the substrate 11. The resistive heating element 13 looses heat by forced convection to the flowing gas and by lateral heat conduction through the membrane 12, and through the fluid to the substrate 11 and the lid 15. Heat conduction to the substrate 11 is minimized by reducing the cross section for heat transfer with the thin support membrane 12 and by using a material such as silicon nitride with a low thermal conductivity as the membrane material.

As shown in FIG. 1a, the resistive heating element 13 can be disposed on the side of the suspended membrane 12 having the sorptive material 14 that is exposed to the flow channel 16. In this embodiment, the lid 15 can be a cap-like structure mounted on the suspended membrane 12. Alternatively, as shown in FIG. 1b, the resistive heating element 13 can be disposed on the side of the suspended membrane 12 opposite the side having the sorptive material 14 that is exposed to the flow channel 16. In this embodiment, the lid 15 can be a mesa-like structure that protrudes into the etch cavity to form the flow channel 16.

Many electrically-conductive materials can be used for the resistive heating element 13. Preferably, the resistive heating element 13 should be made of an electrically-conductive material that is compatible with the chemical environment of a chemical preconcentrator, flow sensing requirements of a thermal anemometer, and can be fabricated with MEMS technologies. Assuming a linear relation between temperature and resistance, the resistance R of the resistive heating element 13 can be represented as $$R = R_r[1 + \alpha(T - T_r)]$$

where T is the temperature of the resistive heating element 13, $R_r$ is the resistance at a reference temperature $T_r$, and $\alpha$ is the temperature coefficient of resistance. For sensitive flow measurement, the resistive heating element 13 should have a suitably high temperature coefficient of resistance. A temperature coefficient of resistance of on the order of 2500–3000 ppm/°C. or higher are preferable, although adequate sensitivity can be obtained with a temperature coefficient of resistance of 1500 ppm/°C. or below. The material should preferably also have a high electrical resistivity and low thermal conductivity. Platinum, tungsten, and other refractory metals and alloys have high temperature coefficients of resistance and other material properties that make them preferable for the resistive heating element 13.

Figure 2:
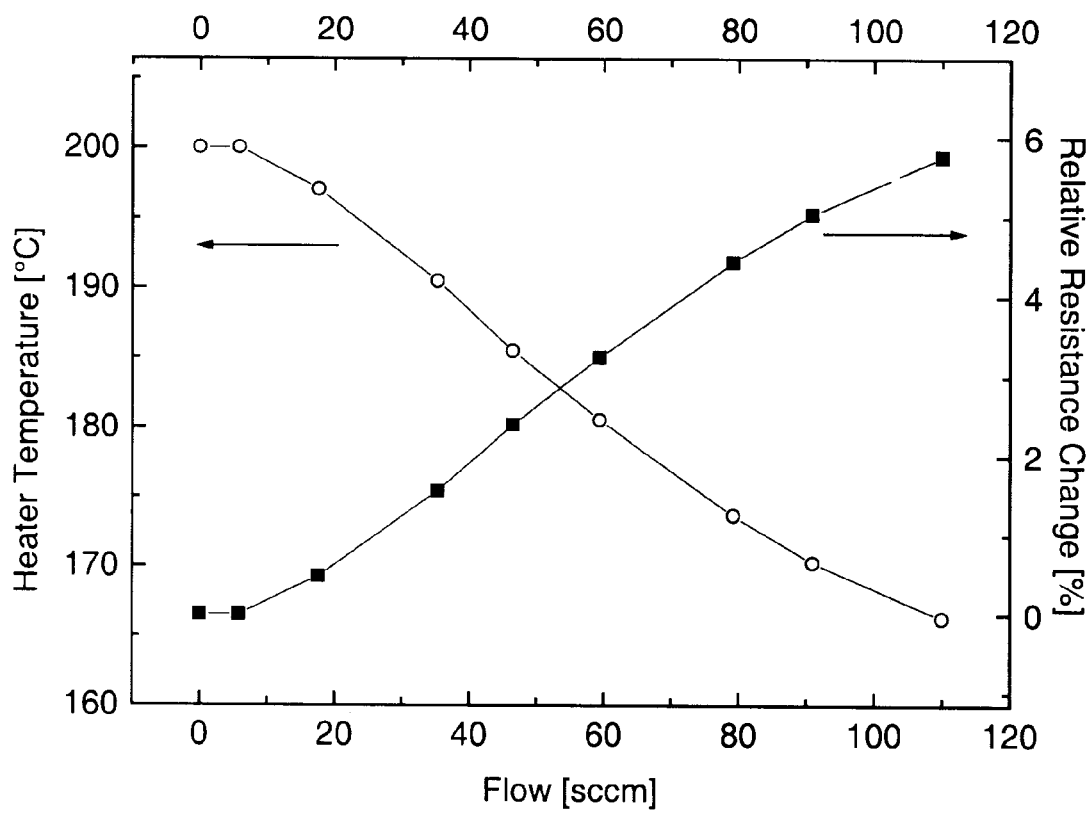
FIG. 2 shows the relationship between temperature of the resistive heating element and fluid flow rate when the thermal flow sensor is operated in the constant voltage mode.

FIG. 2 shows the relationship between the temperature of the resistive heating element 13 and the flow rate of air through the chemical preconcentrator 10 when the thermal flow sensor 19 is operated in the constant voltage mode. In this mode, the thermal flow sensor 19 measures the flowinduced temperature modulation of the resistivity of the resistive heating element 13. To measure the temperature versus flow rate relationship, the gas inlet 17 of the chemical preconcentrator 10 was attached to a flow meter and the gas outlet 18 was attached to a vacuum pump through a needle valve for flow control. As the gas flow rate through the chemical preconcentrator 10 is increased, heat loss due to forced convection to the gas is increased, thereby decreasing the temperature of the resistive heating element 13. The temperature change thereby results in a decrease in the resistivity of the resistive heating element 13, related to the temperature through the known thermal coefficient of resistance of the resistive heater element material. The relative magnitude of this decrease in resistance with flow rate is also shown in FIG. 2. At very low flow rates, the thermal flow sensor 19 becomes less sensitive to the flow because heat conduction to the substrate 11 and lid 15 becomes dominant over heat convection to the flowing gas.

Figure 3:
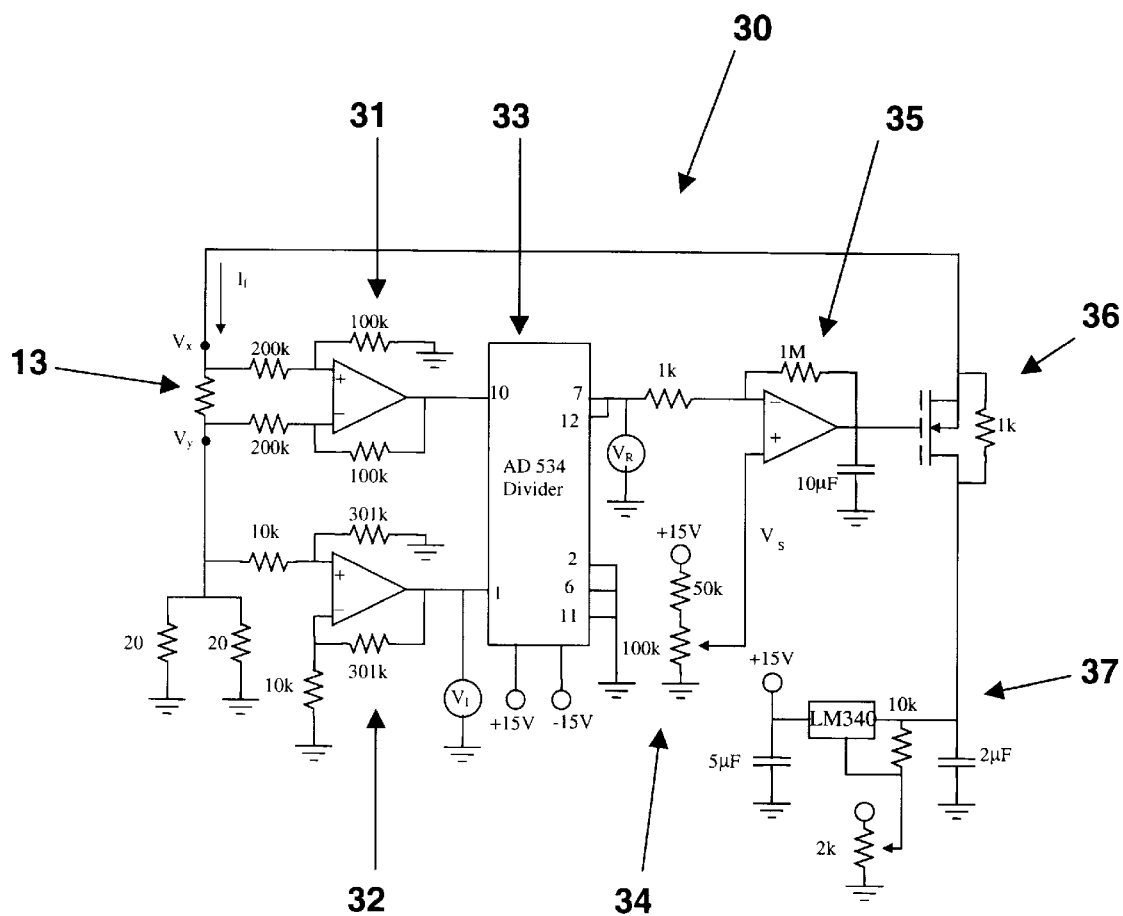
FIG. 3 shows a feedback control circuit for maintaining a constant resistance of the resistive heating element when the thermal flow sensor is operated in the constant temperature mode.

A variety of electronic control circuits can be used to maintain constant voltage or constant temperature of the thermal flow sensor 19. FIG. 3 shows a feedback control circuit 30 for operation of the thermal flow sensor 19 in the constant temperature mode. Since the temperature coefficient of resistance of materials is well known, constant average temperature operation is equivalent to constant resistance operation. In the constant temperature mode, the feedback control circuit 30 measures the power (or current) necessary to maintain the resistive heating element 13 at a constant, set-point temperature. A first operational amplifier 31 measures the voltage through the resistive heating element 13. A second operational amplifier 32 produces a voltage $V_I$ that is proportional to the current $I_f$ through the resistive heating element 13. Therefore, the output voltage $V_R$ of divider 33 (e.g., an Analog Devices AD 534 chip) is proportional to the resistance of the resistive heating element 13. Using differential amplifier 35, $V_R$ can be compared to a set point voltage $V_S$ that can be provided from a voltage divider 34 or from an external source such as a D-to-A converter. The set-point voltage $V_S$ determines the desired constant resistance (i.e., temperature) of the resistive heating element 13. The comparator output of the differential amplifier 35 controls the gate of transistor 36 that feeds back to the resistive heating element 13 to maintain the set point resistance. The larger the difference between the divider voltage $V_R$ and the set-point voltage $V_S$, the greater the feedback current $I_f$ that is switched from power supply 37 to the resistive heating element 13.

Figure 4:
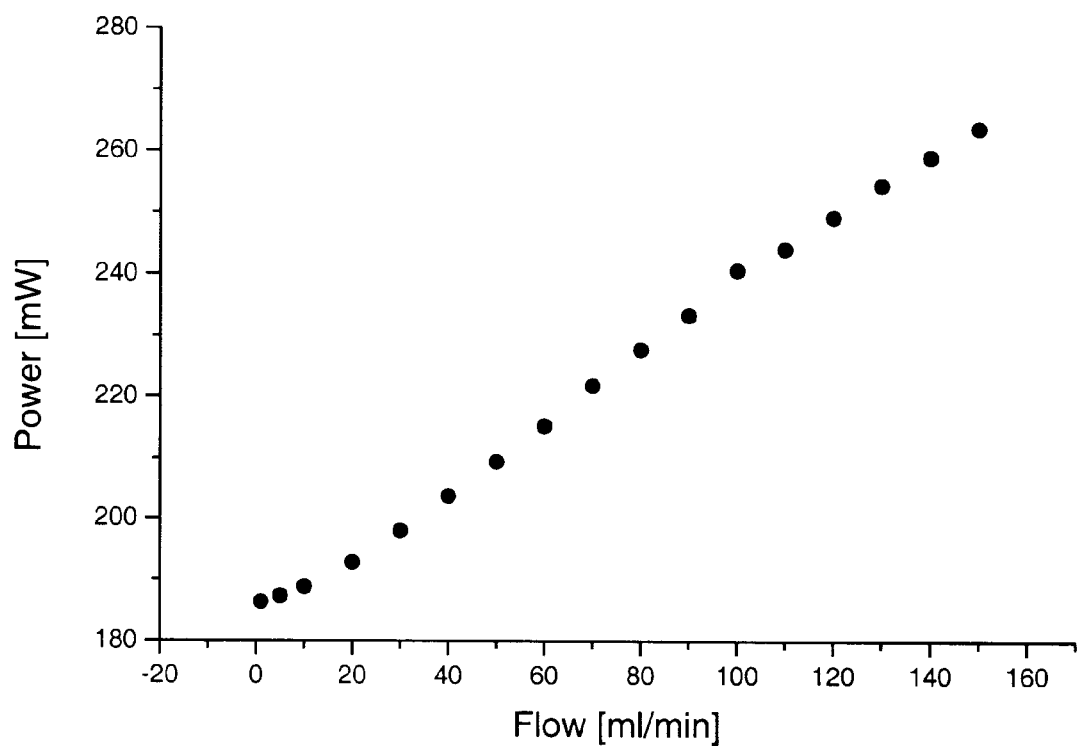
FIG. 4 shows the relationship between the heater power and the fluid flow rate when the thermal flow sensor is operated in the constant temperature mode.

FIG. 4 shows the flow sensitivity of the thermal flow sensor 19 when operated in the constant temperature mode. In this mode, the power required to maintain a constant flow sensor temperature (i.e., resistance) was measured as a function of flow rate of air through the chemical preconcentrator 10. The resistive heating element 13 was maintained at a constant average temperature of 200° C. for these measurements. In contrast with the constant voltage mode, constant temperature operation maintains similar heat conduction conditions throughout the flow range. Because conductive heat loss remains constant and heat loss is controlled by convective heat transfer to the flowing gas in the constant temperature mode of operation, the power required varies nearly linearly with the flow rate. The flow sensitivity is about 0.6 mW/ml/min in the linear range.

Figure 5:
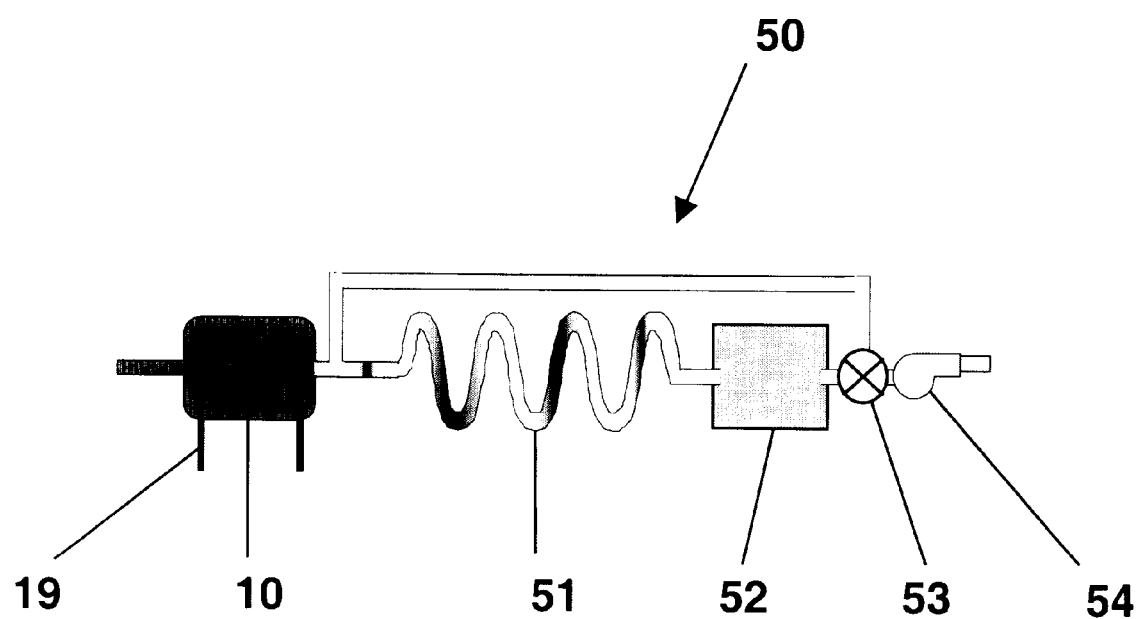
FIG. 5 shows a schematic illustration of a microanalytical system having a chemical preconcentrator with integral thermal flow sensor.

FIG. 5 shows an application of the thermal flow sensor 19 to the measurement of flow in a microanalytical system 50 of the type used in a portable analyzer. The microanalytical system 50 comprises the chemical preconcentrator 10, a microfabricated gas chromatograph column 51, a chemical detector 52, a miniature three-way valve 53, and a miniature pump 54.

Figure 6:
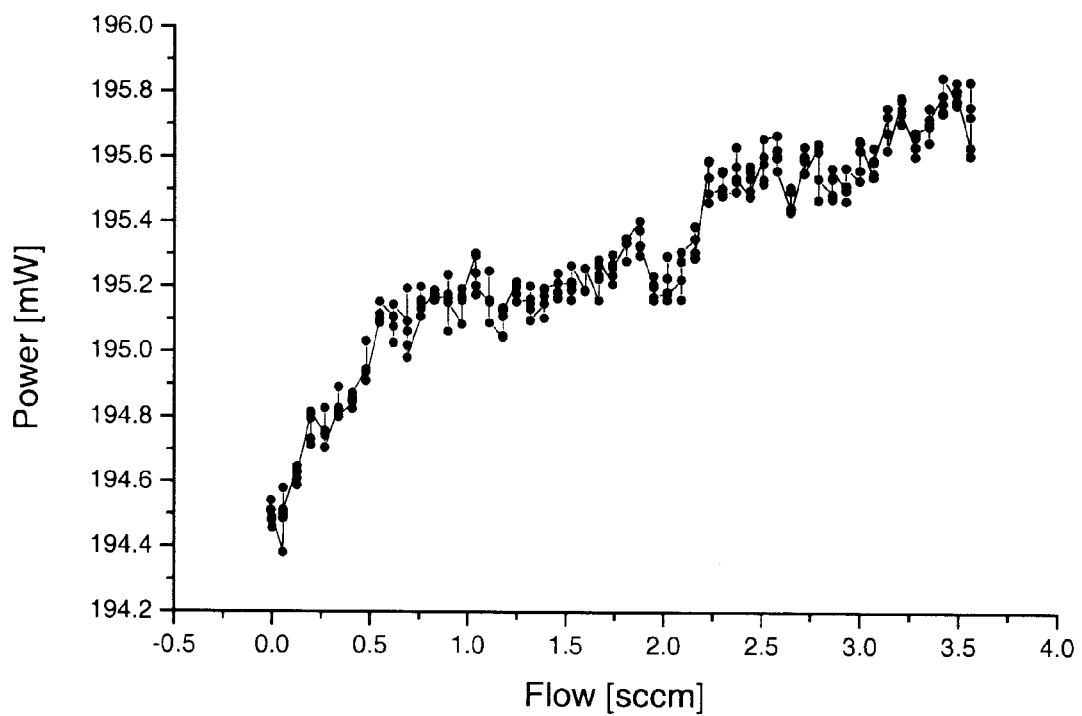
FIG. 6 shows the flow sensitivity at low fluid flow rates when the chemical preconcentrator with integral thermal flow sensor is attached to the microanalytical system.

FIG. 6 shows the power required as a function of flow rate when the chemical preconcentrator 10 is attached to the microfabricated gas chromatograph column 51 and the thermal flow sensor 19 is operated in the constant temperature mode. For the low flow measurements shown in FIG. 6, the temperature of the resistive heating element 13 was maintained at 200° C. The low flow rate observed in this data was due to the large flow restriction from the 86-cm long gas chromatograph column 51 that was placed between the chemical preconcentrator 10 and the pump 54. The thermal flow sensor 19 required about 194.5 mW of power at no flow to maintain the sensor temperature. At very low flows, conduction to the substrate 11 and lid 15 dominates over convective heat transport to the gas. Nonetheless, the thermal flow sensor 19 can have high flow sensitivity because heat conduction from the resistive heating element 13 to the surroundings can be small, the heat capacity of the membrane 12 can be low, and the thermal coefficient of resistance of the resistive heating element material can be high. In particular, the data in FIG. 6 shows that the thermal flow sensor 19 can have flow sensitivity even at the low flow rates that can sometimes be found in a microanalytical system 50.

Figure 7:
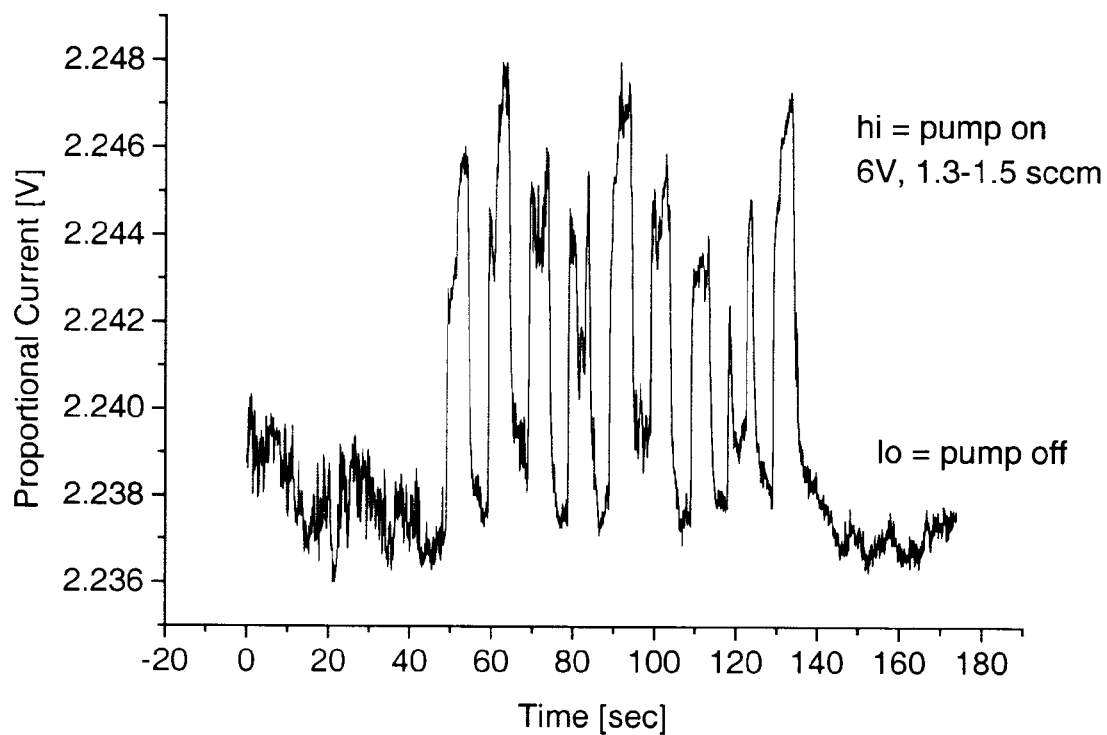
FIG. 7 shows the response time of the thermal flow sensor when the chemical preconcentrator with integral thermal flow sensor is attached to the microanalytical system.

The response time of the thermal flow sensor 19 can also be short because of its small size. FIG. 7 shows that the thermal flow sensor 19 can easily detect 5 second on and off periods of the pump 54. These results show about 8 mV of shift in proportional current out of a baseline value of 2.2V. This shift can be accurately measured with a conventional 16-bit A-to-D converter. Rapid detection of the flow rate enables real-time correction of the chemical analysis obtained from the microanalytical system 50.

Other embodiments of the chemical preconcentrator with integral thermal flow sensor are possible according to the present invention. For example, a three-wire thermal flow sensor configuration can be fabricated. With the three-wire thermal flow sensor, three monolithically integrated microhotplates can be oriented colinearly in the flow path that can both measure flow speed and detect flow direction. In addition, the three-wire sensor can provide a differential signal to eliminate common disturbances, such as temperature drifts. The central microhotplate can be heated, while the upstream and downstream microhotplates measure heat lost and heat gained, respectively, as a result of forced convection. The temperature difference between the upstream and downstream devices is proportional to the square-root of the flow speed.

The embodiments of the present invention have been described as a chemical preconcentrator with an integral thermal flow sensor. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A chemical preconcentrator with integral thermal flow sensor, comprising:
   a substrate having a suspended membrane formed thereon;
   at least one resistive heating element, comprising an electrically-conductive material whose resistance varies with temperature, disposed on a surface of the suspended membrane, and wherein the suspended membrane is exposed to a flow channel of the chemical preconcentrator; and
   a control circuit for heating the resistive heating element to a set temperature and measuring the power required to maintain the resistive heating element at the set temperature when a fluid flows in the flow channel.

2. The chemical preconcentrator of claim 1, wherein the electrically-conductive material has a thermal coefficient of resistance of greater than 1500 ppm/°C.

3. The chemical preconcentrator of claim 1, wherein the electrically-conductive material has a thermal coefficient of resistance of greater than 3000 ppm/°C.

4. The chemical preconcentrator of claim 1, wherein the electrically-conductive material is a metal or semiconductor.

5. The chemical preconcentrator of claim 1, wherein the electrically-conductive material is a refractory metal or refractory metal alloy.

6. The chemical preconcentrator of claim 1, wherein the suspended membrane is selected from the group of silicon-based materials consisting of silicon nitride, polycrystalline silicon, silicon oxynitride, and silicon carbide.

7. The chemical preconcentrator of claim 1, further comprising a sorptive material disposed on the surface of the suspended membrane exposed to the flow channel.

8. The chemical preconcentrator of claim 1, wherein the at least one resistive heating element is disposed on the surface of the suspended membrane exposed to the flow channel.

9. The chemical preconcentrator of claim 1, wherein the at least one resistive heating element is disposed on the surface of the suspended membrane opposite to the flow channel.

10. A chemical preconcentrator with integral thermal flow sensor, comprising:

a substrate having a suspended membrane formed thereon;

at least one resistive heating element, comprising an electrically-conductive material whose resistance varies with temperature, disposed on a surface of the suspended membrane and wherein the suspended membrane is exposed to a flow channel of the chemical preconcentrator; and a control circuit for applying a set voltage across the resistive heating element and measuring the resistance of the resistive heating element when a fluid flows in the flow channel.

11. The chemical preconcentrator of claim 10, wherein the electrically-conductive material has a thermal coefficient of resistance of greater than 1500 ppm/°C.

12. The chemical preconcentrator of claim 10, wherein the electrically-conductive material has a thermal coefficient of resistance of greater than 3000 ppm/°C.

13. The chemical preconcentrator of claim 10, wherein the electrically-conductive material is a metal or semiconductor.

14. The chemical preconcentrator of claim 10, wherein the electrically-conductive material is a refractory metal or refractory metal alloy.

15. The chemical preconcentrator of claim 10, wherein the suspended membrane is selected from the group of silicon-based materials consisting of silicon nitride, polycrystalline silicon, silicon oxynitride, and silicon carbide.

16. The chemical preconcentrator of claim 10, further comprising a sorptive material disposed on the surface of the suspended membrane exposed to the flow channel.

17. The chemical preconcentrator of claim 10, wherein the at least one resistive heating element is disposed on the surface of the suspended membrane exposed to the flow channel.

18. The chemical preconcentrator of claim 10, wherein the at least one resistive heating element is disposed on the surface of the suspended membrane opposite to the flow channel.

* * * * *